United States Patent
Blanck et al.

(10) Patent No.: US 6,866,169 B2
(45) Date of Patent: Mar. 15, 2005

(54) APPARATUS FOR RELEASING DIFFERING AMOUNTS OF AN AIR FRESHENER FROM A CONTAINER

(75) Inventors: Arnauld Blanck, Ivry s/ Seine (FR); Marc Pinon, Paris (FR); Christophe Rebours, Chatou (FR)

(73) Assignee: S. C. Johnson & Son, Inc., Racine, WI (US)

( * ) Notice: Subject to any disclaimer, the term of this patent is extended or adjusted under 35 U.S.C. 154(b) by 94 days.

(21) Appl. No.: 10/434,059

(22) Filed: May 9, 2003

(65) Prior Publication Data

US 2004/0251317 A1 Dec. 16, 2004

(51) Int. Cl.⁷ .............................................. B65D 83/00
(52) U.S. Cl. .................. 222/402.13; 239/337
(58) Field of Search .................. 222/402.13, 402.15, 222/321.6; 239/337, 340, 541, 578

(56) References Cited

U.S. PATENT DOCUMENTS

| | | | |
|---|---|---|---|
| 4,187,963 A | * | 2/1980 | Mascia .................. 222/402.13 |
| 5,862,960 A | | 1/1999 | Miller et al. ................. 222/325 |
| 5,875,934 A | | 3/1999 | Miller et al. ................. 222/183 |

* cited by examiner

*Primary Examiner*—Christopher Kim

(57) ABSTRACT

A dispenser (200) used in conjunction with a conventional replaceable cartridge (100) containing an air freshener. The dispenser (200) includes a first portion (300) and a second portion (400). The first portion (300) is actuatable and includes a diaphragm (350) and a step (351). The second portion (400) is actuatable and includes a flat ring (460) arranged proximate to the step (351) of the first portion (300). When the first portion (300) is actuated, the diaphragm (350) contacts a nozzle (130) of the conventional container (100), thereby releasing a first amount of air freshener. When the second portion (400) is actuated, the diaphragm (350) of the first portion (300) is forced over a portion of the nozzle (130) such that the flat ring (460) of the second portion (400) contacts the nozzle (130), thereby releasing a second amount of air freshener.

11 Claims, 6 Drawing Sheets

APPARATUS FOR RELEASING DIFFERING AMOUNTS OF AN AIR FRESHENER FROM A CONTAINER

BACKGROUND OF THE INVENTION

1. Field of the Invention

Our invention relates generally to an apparatus to be used with a conventional container, which allows for selectively dispensing a desired amount of the contents within the container to the atmosphere. More particularly, our invention relates to a dispenser for dispensing air freshener from a replaceable cartridge. The dispenser allows a user to select one of at least two amounts of air freshener to be released.

2. Description of the Related Art

Air fresheners have many household uses, and over the years, dispensers for air fresheners have been designed having a myriad of shapes and sizes.

Of these varied dispensers, those skilled in the art are generally aware of dispensers that accept a replaceable container filled with the air freshener. For example, the device sold by S.C. Johnson & Son, Inc., of Racine, Wis., under the trademark "Press 'n Fresh™" is a commercial product designed to mount on a vertical surface and to dispense concentrated air freshener from a replaceable container. Such a replaceable container containing the air freshener is of standard proportions and composition and generally includes an actuatable valve stem that, when displaced toward the container, releases air freshener from within the container, through the valve stem. Because the container can be purchased separately, there is no need to replace the dispenser upon dissemination of all of the air freshener contained therein.

Another type of air freshener dispenser that accepts a replaceable cartridge is shown in U.S. Pat. No. 5,862,960 to Miller et al. (incorporated herein by reference). Of pertinence, the Miller et al. patent illustrates a nozzle device attached to the container and arranged proximate to the valve stem of the container. The nozzle device provides an increased surface area upon which an actuating force may be applied. When the actuating force is applied to the nozzle device, air freshener is released through the valve stem, and out an opening in the nozzle.

While such methods of releasing air freshener from within a container are generally known, there is still a need in the art for a device that allows a user to release a selectively varied amount of air freshener from a conventional container. Specifically, because more air freshener is required in some instances than in others, an air freshener dispenser is desired, which allows a user to vary the amount of air freshener released into the atmosphere.

SUMMARY OF THE INVENTION

Our invention provides a versatile apparatus that addresses at least the problems noted above.

According to one aspect, our invention provides a dispenser for use with a container having a nozzle such that when the nozzle is actuated, a desired amount of the contents of the container is released from within the container. The dispenser includes an actuatable first portion and an actuatable second portion. The actuatable first portion has a diaphragm arranged proximate to the nozzle of the container with an aperture therethrough and a step depending from the diaphragm. When the first portion is actuated, a portion of the diaphragm actuates the nozzle, thereby releasing a first amount of the contents of the container. The second portion has a flat ring with an aperture therethrough arranged proximate to the step of the first portion. When the second portion is actuated, the second portion contacts the step of the first portion, thereby displacing the first portion so that at least a portion of the nozzle passes through the aperture in the diaphragm of the first portion and the flat ring of the second portion actuates the nozzle, thereby releasing a second amount of the contents of the container.

According to another aspect, our invention provides a dispenser for use with a container containing an air freshener, the container including an actuatable nozzle that effects the release of an amount of the air freshener from within the container. The dispenser includes an actuatable first portion and an actuatable second portion. The actuatable first portion includes a diaphragm having an aperture and a plurality of cutouts therethrough forming plural ribs, and a step depending from the diaphragm. The actuatable second portion includes a flat ring with an aperture therethrough arranged proximate to the step of the first portion. When the first portion is actuated, at least a portion of the ribs of the diaphragm contacts an actuation surface of the nozzle of the container, effecting the release of a first amount of the air freshener. When the second portion is actuated, the actuation surface of the nozzle is forced through the aperture of the diaphragm of the first portion so that the flat ring of the second portion contacts the actuation surface of the nozzle of the container, effecting the release of a second amount of the air freshener.

A better understanding of these and other features and advantages of our invention may be had by reference to the drawings and to the accompanying detailed description of the preferred embodiments, in which preferred embodiments of the invention are illustrated and described.

BRIEF DESCRIPTION OF THE DRAWINGS

Throughout the figures, like or corresponding reference numerals designate like or corresponding parts.

DETAILED DESCRIPTION OF THE PREFERRED EMBODIMENTS

Figure 1:
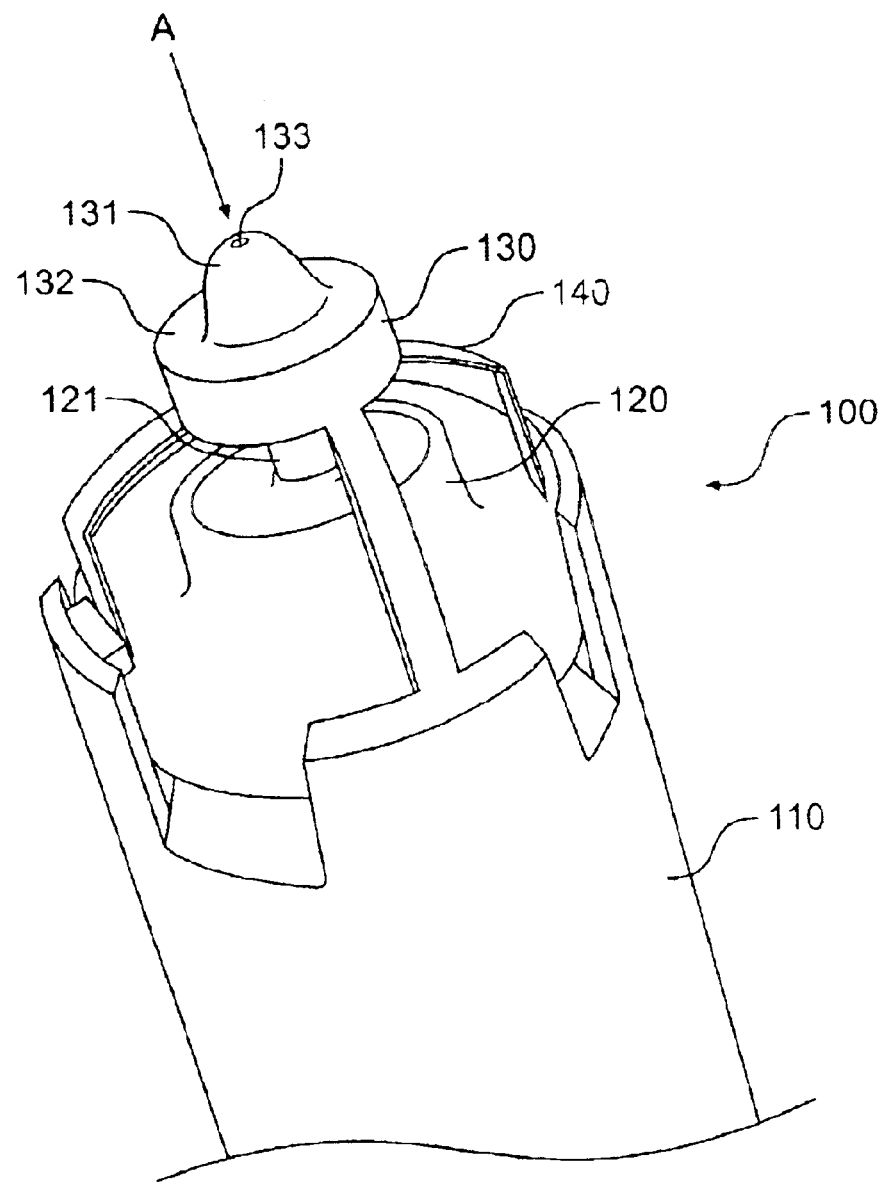
FIG. 1 is a perspective view of a conventional replaceable air freshener cartridge.

FIG. 1 illustrates a replaceable cartridge 100 containing an air freshener (not shown). (While this specification will discuss our invention solely in terms of its use in conjunction with an air freshener, it is understood that conventional containers containing other pressurized products, e.g., insect repellant, fragrances, and the like, may also be used.) As shown, the conventional container 100 generally includes a main body 110, a valve assembly 120, and a nozzle 130.

The main body 110 may be one of many shapes and sizes. While these different shapes and sizes may be used with different dispensers, it is only required that the main body 110 form a cavity in which a pressurized air freshener is contained.

The valve assembly 120 is attached to a distal end of the main body 110. The valve assembly 120 includes a valve stem 121. The valve stem 121 is actuatable in a direction toward the main body 110 (shown by arrow A in FIG. 1). Put another way, the valve stem 121 can be displaced into the main body 110. When so actuated, a valve (not shown) in the valve assembly 120 opens and the pressurized air freshener contained within the main body 110 is released through the valve stem 121.

The nozzle 130 is arranged proximate to the valve stem 121 and includes a tip 131, an actuation surface 132, and an opening 133. The tip 131 protrudes from the nozzle 130 in a direction opposite to the main body 110 of the container 100. The actuation surface 132 is arranged substantially perpendicular to the actuation direction (arrow A) of the valve stem 121 and preferably extends radially outwardly from a base of the tip 131. When a sufficient force is applied to the actuation surface 132 in the direction of arrow A, the nozzle 130 contacts and actuates the valve stem 121, thereby releasing an amount of the air freshener from within the main body 110 of the container 100. The opening 133 of the nozzle 130 extends through the tip 131 of the nozzle 130 to allow the air freshener released from the main body 110 to pass through the nozzle 130, out the opening 133 and into the atmosphere.

The nozzle 130 is maintained proximate to the valve stem 121 by a plurality of supporting arms 140. The supporting arms 140 are preferably flexible so that when the nozzle 130 is displaced due to actuation, the supporting arms 140 will flex to maintain the desired orientation of the nozzle 130.

Figure 2:
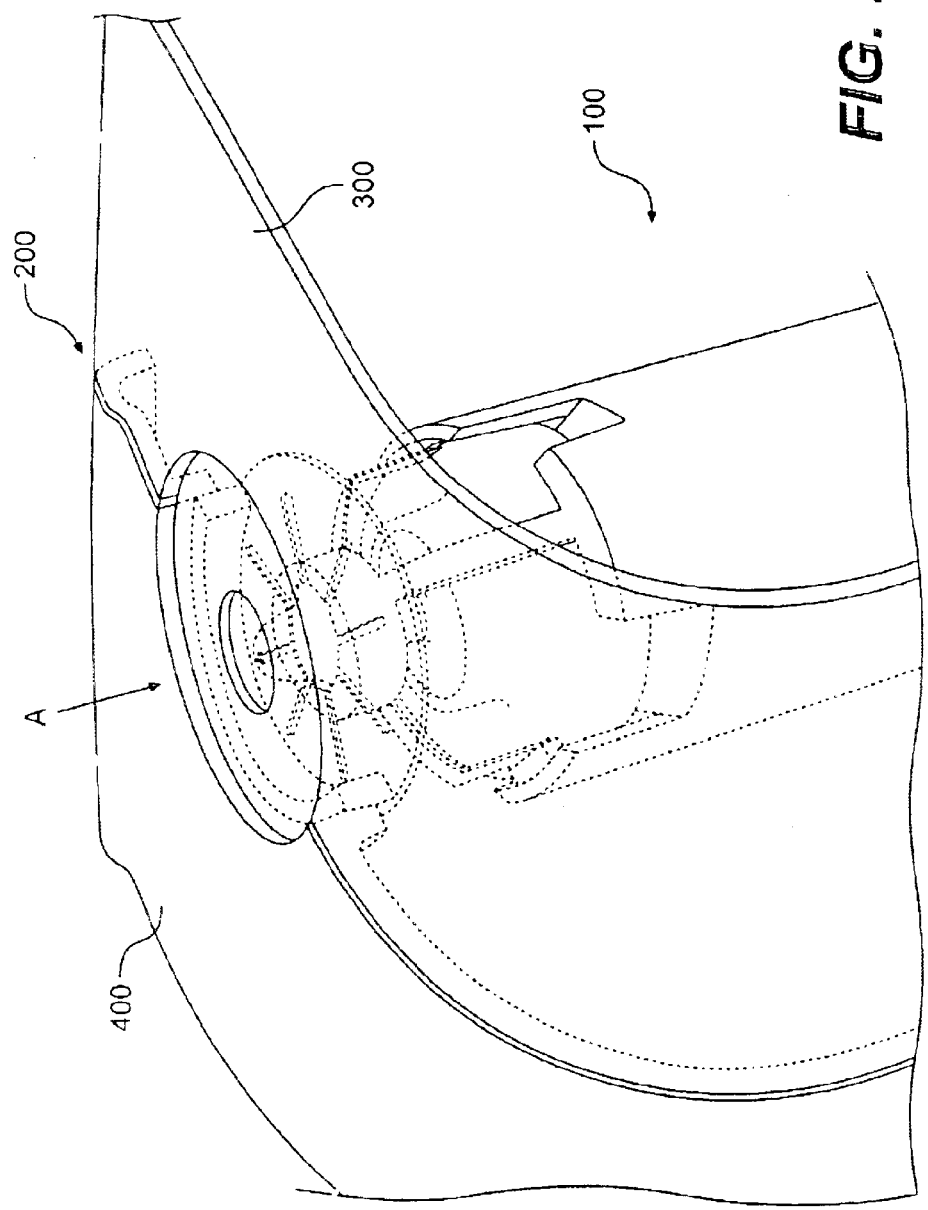
FIG. 2 is a partial cut-away, perspective view of a dispenser according to a first embodiment of our invention, attached to the conventional replaceable cartridge shown in FIG. 1. The dispenser includes a first portion and a second portion.

FIG. 2 illustrates a preferred embodiment of our invention. Generally, in this embodiment, a dispenser 200 includes a first portion 300 and a second portion 400. The dispenser 200 is arranged proximate to a replaceable cartridge 100 for effectuating release of the air freshener contained within the replaceable cartridge 100.

Figure 3:
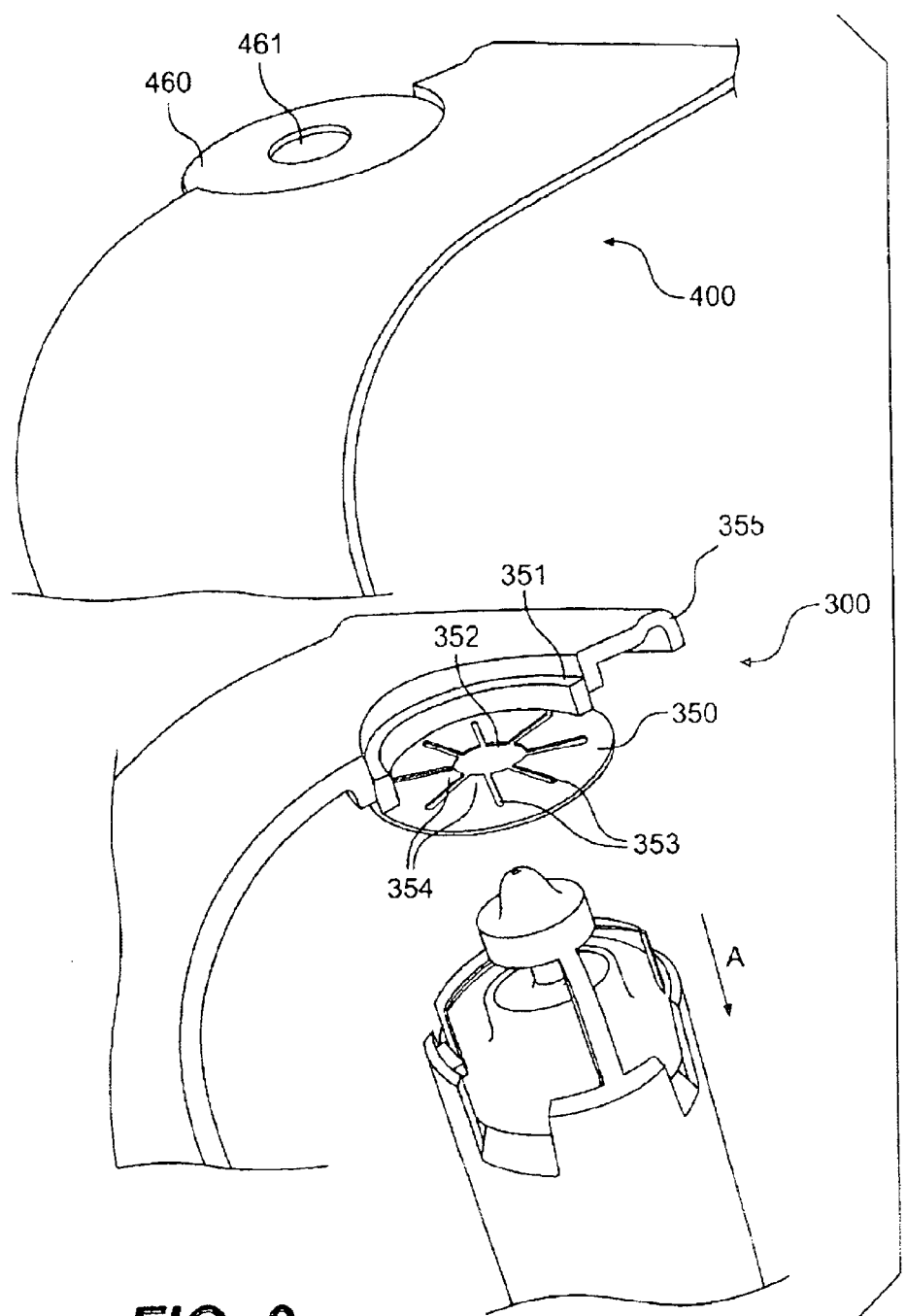
FIG. 3 is an exploded view of the embodiment or FIG. 2.

FIG. 3 is an exploded view of the embodiment of FIG. 2. As can be seen in FIG. 3, the first portion 300 of the dispenser 200 includes a diaphragm 350 and a step 351. In a preferred embodiment, the diaphragm 350 is substantially circular in shape and includes a substantially circular aperture 352 therethrough. The aperture 352 is substantially concentric with the diaphragm 350. The aperture 352 is larger in diameter than the tip 131 of the nozzle 130, but is sized such that at least a portion of the diaphragm 350 is disposed above the actuation surface 132 of the nozzle 130. As such, if an actuation force is applied to the diaphragm 350 in the direction of arrow A, at least a portion of the diaphragm 350 will contact the actuation surface 132 of the nozzle 130, thus actuating the valve stem 121 and releasing air freshener. Also as shown in FIG. 3, the diaphragm 350 includes a plurality of slots 353 extending radially outwardly from the aperture 352 of the diaphragm 350. The slots 353 extend through the diaphragm 350, leaving a plurality of ribs 354 between the slots 353. Because of this configuration, when an actuation force is applied to the diaphragm 350 in the direction of arrow A, the ribs 354 flex. To further aid in this flexing, the diaphragm 350 is preferably made of a flexible material.

Also, the first portion 300 includes a step 351. As shown in FIG. 3, the step 351 is generally semicircular and extends axially from the diaphragm 350. The step 351 is substantially concentric with the diaphragm 350 and the aperture 352 of the diaphragm 350. The step 351 is connected to the remainder of the first portion 300. The function of the step 351 will be discussed in detail below, in conjunction with FIGS. 4A through 4C.

FIG. 3 also illustrates the second portion 400 of our preferred dispenser 200. As shown, the second portion 400 includes a flat ring 460 that is substantially circular in shape. The flat ring 460 includes a substantially circular aperture 461 that is substantially concentric with the flat ring 460. The aperture 461 through the flat ring 460 is larger in diameter than the tip 131 of the nozzle 130, but is sized such that if the flat ring 460 were slid over the tip 131 of the nozzle 130, at least a portion of the flat ring 460 would contact the actuation surface 132 of the nozzle 130. As shown in FIG. 2, when the second portion 400 of the dispenser 200 is assembled with the first portion 300 of the dispenser 200, the flat ring 461 is designed to sit on the step 351 of the first portion 300.

Figure 4A:
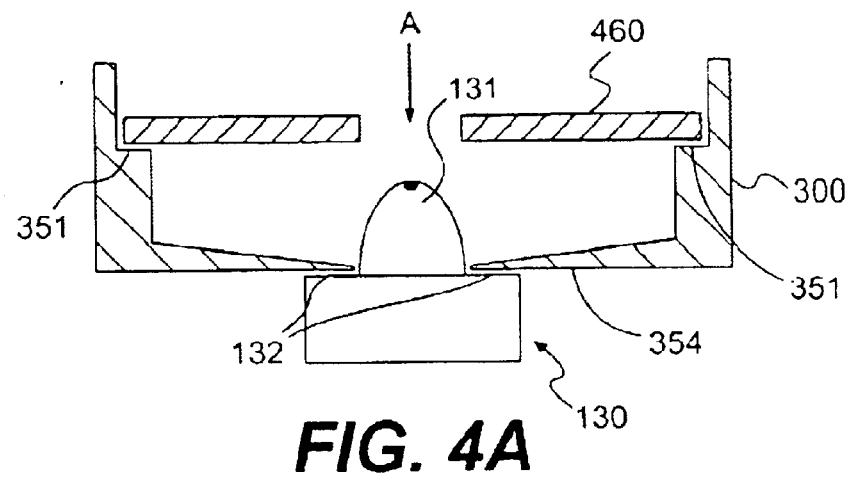
FIG. 4A is a cross-sectional view of the embodiment of FIG. 2.
Figure 4B:
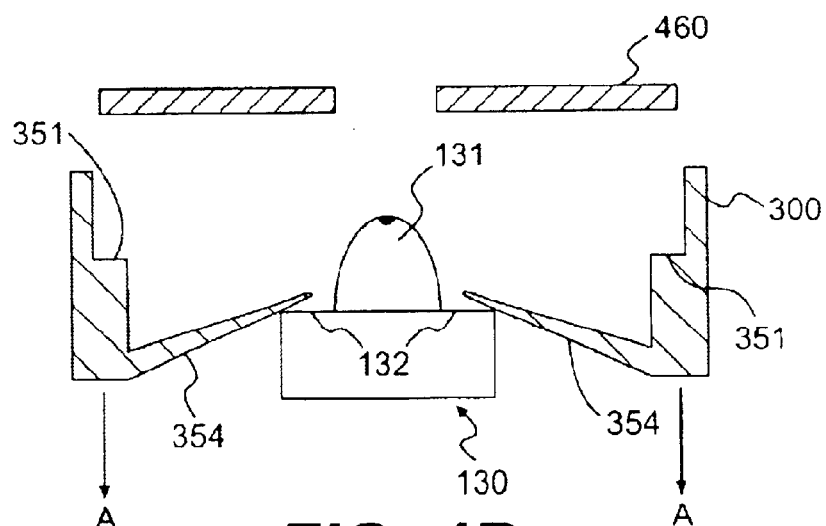
FIG. 4B is a cross-sectional view of the embodiment of FIG. 2, with an actuating force applied to the first portion.
Figure 4C:
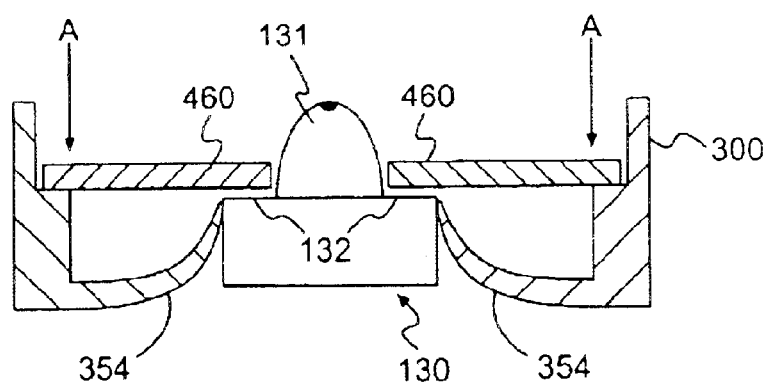
FIG. 4C is a cross-sectional view of the embodiment of FIG. 2, with an actuating force applied to the second portion.

Having thus generally described the components of a preferred embodiment of our invention, FIGS. 4A through 4C will be used for further clarification and to explain the operation of our dispenser 200. Each of FIGS. 4A, 4B, and 4C shows a cross-sectional view of the assembled relationship among the nozzle 130, the first spray portion 300, and the flat ring 460 of the second spray portion 461. For clarity, many components have been omitted from these figures.

FIG. 4A depicts the at-rest, non-actuated position. As can be seen, the diaphragm 350, specifically, the ribs 354 of the diaphragm 350, is arranged proximate to the actuating surface 132 of the nozzle 130, and the flat ring 460 of the second portion 400 is proximate to the step 351 of the first portion 300. The diaphragm 300 may or may not be contacting the actuating surface 132 of the nozzle 130 and the flat ring 460 of the second portion 400 may or may not be contacting the step 351 of the first portion 300.

FIG. 4B shows the operation to release a first amount of air freshener, resulting from an actuation force being applied to the first portion 300 in the direction of arrow A. Through application of this force, the diaphragm 350 contacts the actuating surface 132 of the nozzle 130, thereby displacing the nozzle 130 toward the container 100 and effecting a release of a first amount of air freshener through the opening 133 in the nozzle 130. As illustrated, the ribs 354 of the diaphragm 350, upon contacting the actuating surface 132 of the nozzle 130, partly deflect because, as described above, the ribs 354 of the diaphragm 350 are flexible. While the first portion 300, specifically, the diaphragm 350, actuates the nozzle 130, the flat ring 460 of the second portion 400 remains in its at-rest position. Alternatively, the flat ring 460 may be seated on the step 351 of the first portion 300 and remain there throughout the motion of the first portion 300.

When it is desirable that more air freshener be released, our invention is also capable of releasing a second amount of air freshener. As shown in FIG. 4C, when the flat ring 460 of the second portion 400 is actuated in the direction of arrow A, the flat ring 460 contacts the step 351 of the first portion 300. As a result, the diaphragm 300 applies a force to the actuating surface 132 of the nozzle 130, thus releasing air freshener, as in the arrangement shown in FIG. 4B. Different than the arrangement shown in FIG. 4B, however, the flat ring 460 continues to displace the first portion 300 such that the ribs 354 of the diaphragm 350 push over and past the nozzle 130 to a point at which they contact only the outer diameter of the nozzle 130, and the flat ring 460 of the second portion 400 contacts the actuating surface 132. As should be apparent, a continued application of force on the flat ring 460 of the second portion 400 will displace the nozzle 130 further, thereby effecting a release of a second amount of air freshener from the container 100.

Figure 5A:
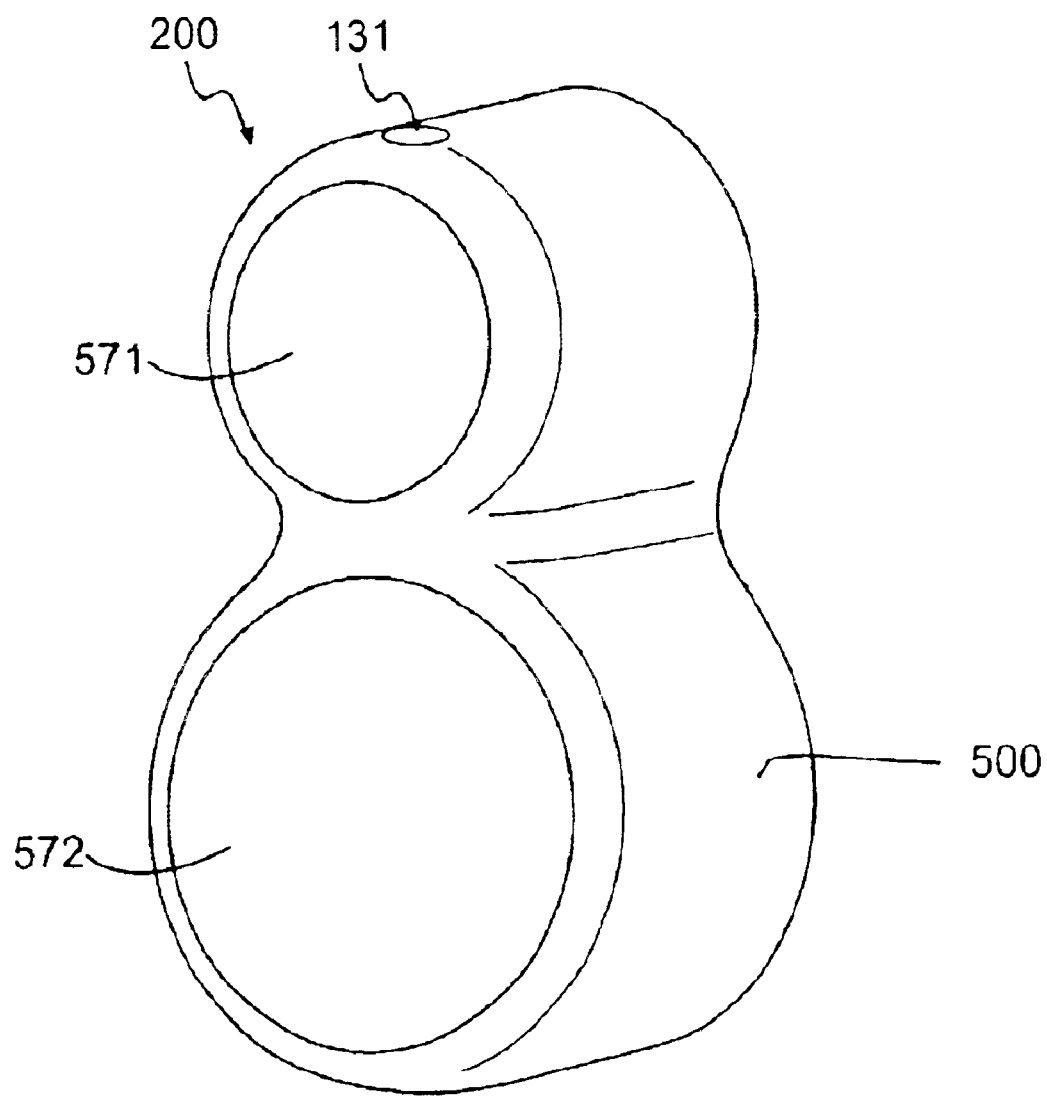
FIG. 5A is a perspective view of a commercial embodiment of our invention.
Figure 5B:
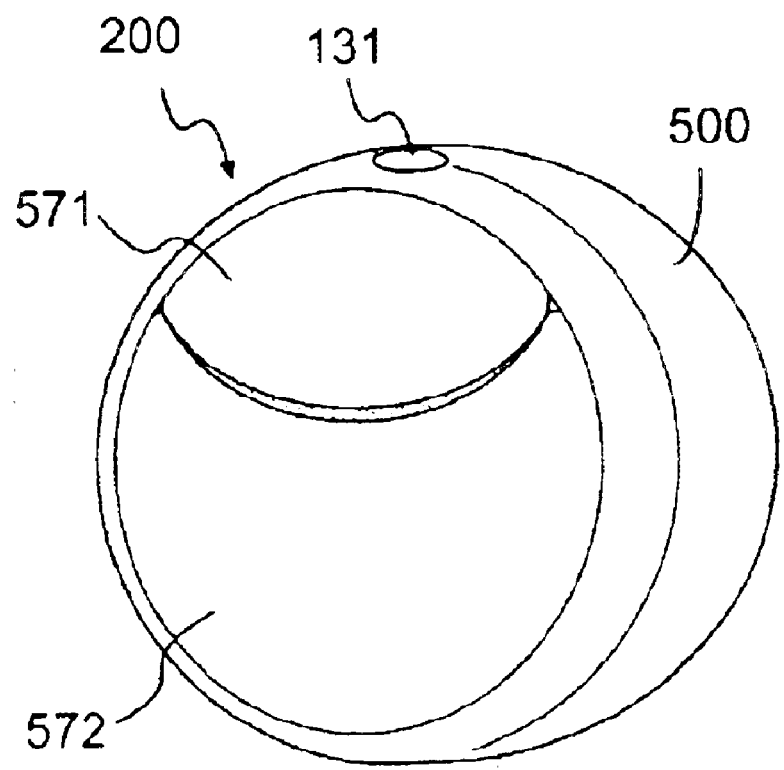
FIG. 5B is a perspective view of another commercial embodiment of our invention.

As should now be apparent, our invention entails a novel air freshener dispenser that allows a user to release multiple amounts of air freshener. A user can determine the appropriate amount of air freshener to be released and then actuate either the first portion or the second portion to release the desired amount. As shown, for example, in FIGS. 5A and 5B, in commercial embodiments of our dispenser 200, a housing 500 and two buttons 571, 572 can be provided, each of the buttons mechanically communicating with one of the first portion 300 and the second portion 400 of our dispenser 200. For example, in these embodiments, a smaller button 571 is mechanically connected to the first portion 300 and a larger button 572 is mechanically connected to the second portion 400. By mechanically connected, we mean that by pressing the smaller button 571, the first portion 300 will be actuated, thus releasing a first amount of air freshener, and by pressing the larger button 572, the second portion 400 will be actuated, thus releasing a second amount of air freshener.

By way of example, in a preferred embodiment, the mechanical connection works as follows. As shown most clearly in FIG. 3, both the first portion 300 and the second portion 400 are substantially L-shaped, i.e., they each contain a vertical portion extending in a direction generally perpendicular to arrow A and a horizontal portion depending from the vertical portion, generally parallel to arrow A. At a side of the horizontal portion opposite the vertical portion, there is a corner portion 355 (not shown on the second portion 400). Within the casing 500 of the commercial embodiments shown in FIGS. 5A and 5B, there is a pivot (not shown) with which the corner portions of each of the first portion 300 and the second portion 400 interact. As such, when the vertical portion of either the first portion 300 or the second portion 400 is actuated, via pressure on one of the buttons 571, 572, whichever of the first portion 300 or the second portion 400 is pressed, the corner portion thereof rotates about the pivot, thereby moving the horizontal portion in a direction generally parallel to arrow A. Of course, other types of mechanical connections between the buttons 571, 572 and the first and second portions, respectively, to allow the release of air freshener can be used without departing from the scope of the invention.

The embodiments discussed above are representative of preferred embodiments of our invention and are provided for illustrative purposes only. They are not intended to limit the scope of our invention. Although specific shapes, configurations, materials, etc., have been shown and described, such are not limiting. Modifications and variations are contemplated within the scope of our invention, which we intend to be limited only by the scope of the accompanying claims.

We claim:

1. A dispenser for use with a container having a nozzle such that when the nozzle is actuated, a desired amount of the contents of the container is released from within the container, the dispenser comprising:

an actuatable first portion having (i) a diaphragm arranged proximate to the nozzle of the container and having an aperture therethrough and (ii) a step depending from the diaphragm, wherein, when the first portion is actuated, a portion of the diaphragm actuates the nozzle, thereby releasing a first amount of the contents of the container; and an actuatable second portion having a flat ring with an aperture therethrough arranged proximate to the step of the first portion, wherein when the second portion is actuated, the second portion contacts the step of the first portion, thereby displacing the first portion so that at least a portion of the nozzle passes through the aperture in the diaphragm of the first portion and the flat ring of the second portion actuates the nozzle, releasing a second amount of the contents of the container.

2. The dispenser of claim 1, wherein the aperture in the diaphragm is larger in diameter than a tip of the nozzle.

3. The dispenser of claim 2, wherein the diaphragm includes a plurality of cutouts therethrough, extending radially outwardly from the aperture, forming a plurality of ribs between the cutouts.

4. The dispenser of claim 3, wherein the ribs are flexible so that at least a portion of the nozzle can pass through the aperture when the second portion is actuated.

5. The dispenser of claim 1, wherein the aperture through the fat ring of the second portion is larger in diameter than a tip of the nozzle.

6. The dispenser of claim 1, wherein the second amount of the contents of the container is greater than the first amount of the contents of the container.

7. The dispenser of claim 1, further comprising a first button in mechanical communication with the first portion and a second button in mechanical communication with the second portion.

8. The dispenser of claim 7, wherein the first button is smaller than the second button.

9. A dispenser for use with a container containing an air freshener, the container including an actuatable nozzle that effects the release of a desired amount of the air freshener from within the container, the dispenser comprising:

an actuatable first portion including a diaphragm having an aperture and a plurality of cutouts therethrough forming plural ribs, and a step depending from the diaphragm; and an actuatable second portion including a flat ring with an aperture therethrough arranged proximate to the step of the first portion, wherein, when the first portion is actuated, the diaphragm contacts an actuation surface of the nozzle of the container, effecting the release of a first amount of the air freshener, and when the second portion is actuated, the actuation surface or the nozzle is forced through the aperture of the diaphragm of the first portion so that the flat ring of the second portion contacts the actuation surface of the nozzle of the container, effecting the release of a second amount of the air freshener.

10. The dispenser of claim 9, wherein the aperture in the diaphragm is larger in diameter than a tip of the nozzle of the container, but is sized such that at least a portion of the diaphragm contacts the actuation surface of the nozzle when the first portion is actuated.

11. The dispenser of claim 10, wherein the diaphragm flexes when each of the first portion and the second portion is actuated, and flexes sufficiently to allow the actuation surface of the nozzle to pass entirely through the aperture of the diaphragm when the second portion is actuated.

* * * * *